United States Patent [19]
Burns et al.

[11] Patent Number: 5,523,434
[45] Date of Patent: Jun. 4, 1996

[54] SYNTHESIS OF BLEACH ACTIVATORS

[75] Inventors: Michael E. Burns, Hamilton, Ohio; Anthony J. Simpson, Northumberland, United Kingdom

[73] Assignee: The Procter & Gamble Company, Cincinnati, Ohio

[21] Appl. No.: 404,654

[22] Filed: Mar. 15, 1995

[51] Int. Cl.$^6$ .................................................. C07C 231/12
[52] U.S. Cl. .................... 554/68; 554/45; 560/41; 560/142
[58] Field of Search .............................. 554/45, 90, 154, 554/68; 560/142, 41

[56] References Cited

U.S. PATENT DOCUMENTS 4,634,551  1/1987  Burns et al. ............................. 252/102
4,852,989  8/1989  Burns et al. ................................ 8/107

OTHER PUBLICATIONS

*Chemistry of Organic Compounds*, 2nd ed., Noller, p. 549 (1957), Library of Congress Catalog Card No. 57–7045.

*Primary Examiner*—José G. Dees
*Assistant Examiner*—Samuel Barts
*Attorney, Agent, or Firm*—Jerry J. Yetter; Kim William Zerby; Jacobus C. Rasser

[57] ABSTRACT

The synthesis of phenol sulfonate esters of alkanoyl amino acids is conducted in the presence of aqueous base to provide bleach activator compounds. Thus, the acid chloride of N-nonanoyl-6-aminocaproic acid is reacted with the sodium salt of p-phenol sulfonate in the presence of water at a pH in the range of about 9 to about 12 to yield the corresponding phenol sulfonate ester. The synthesis of the phenol sulfonate ester of the mononyl amide of adipic acid is also illustrated.

8 Claims, No Drawings

SYNTHESIS OF BLEACH ACTIVATORS

FIELD OF THE INVENTION

The present invention relates to the chemical synthesis of organic compounds which are useful as activators in fabric bleaches and laundry compositions.

BACKGROUND OF THE INVENTION

The formulation of modem cleaning compositions is a sophisticated and complex undertaking. The formulator is faced with the need to employ ingredients which are safe and effective under a wide variety of usage conditions and with a wide variety of soil and fabric types. For example, some consumers prefer to use laundry detergents at temperatures as low as about 5° C., whereas others use such compositions at temperatures approaching the boil. Soil types range from the particulate silicates and clay soils, thorough carbohydrate soils, proteinaceous soils including body soils, and food stains and other greasy/oily stains. Mixed stains, such as those caused by cosmetics and which comprise both water-insoluble oily materials and highly colored particulates, are also often commonly encountered by the user.

A wide variety of ingredients have been suggested for use in modern cleaning compositions, including various bleaches, surfactants, builders, soil release agents, and the like. While a review of the literature would seem to suggest that such ingredients are widely available, many are specialty items which are not economical for use in the home. Indeed, one of the problems associated with many of the ingredients employed in fabric laundering and bleach compositions is their expense. Many of the more sophisticated ingredients require multi-step reaction sequences which are, themselves, expensive. Moreover, some of the proposed ingredients must be manufactured using organic solvent systems, which must be recovered and recycled in order to minimize costs. In addition, the organic solvent reactions often require high reaction temperatures, which result in a reaction product of poor color. In almost every conceivable circumstance, it is highly preferred to use ingredients which can be economically prepared using as few processing steps as possible. In particular, it is highly preferred to use processing steps which employ water as the primary solvent.

One class of materials which has recently come into commercial use in bleaches and bleaching laundry detergents comprise various, so-called bleach "activators". These organic activator molecules are designed to improve the performance of conventional inorganic bleaching agents such as percarbonate and perborate. Unfortunately, many of the proposed bleach activator molecules are difficult and expensive to prepare, and thus remain mere laboratory curiosities.

By the present invention, certain amido bleach activators are prepared using economical synthetic methods which employ water as one of the principal reaction solvents. Additional benefits of the present invention include the ability to use short reaction times and low reaction temperatures, both of which help achieve reaction products having excellent light or white color.

BACKGROUND ART

The acylation of alcohols and amines in aqueous solution using dilute alkali to combine with hydrogen halide formed is commonly known as the Schotten-Baumann Reaction. See *Chemistry of Organic Compounds,* 2nd ed., Noller, p. 549 (1957), Library of Congress Catalog Card no. 57-7045. Bleach activators of the type provided by the present process are disclosed in U.S. Pat. Nos. 4,634,551 and 4,852,989.

SUMMARY OF THE INVENTION

The present invention encompasses a process for preparing phenol sulfonate esters of hydrocarboyl amino acids, comprising the steps of:

(a) reacting an amino acid of the formula

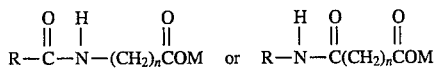

wherein n is from 1 to about 8, M is H or an alkali metal salt, and R is $C_{1-14}$ alkyl, alkenyl, aryl or alkaryl, preferably $C_7$–$C_9$ alkyl, i.e., an alkanoyl amino acid, with an acid halide to prepare the corresponding amino acid halide; and (b) reacting the amino acid halide of step (a) with a phenol sulfonate in the presence of water and base.

Step (a) of the process herein can be conducted using an inorganic acid halide selected from the group consisting of $SOCl_2$, $PCl_3$, $PCl_5$, $POCl_3$ and their corresponding bromides, or oxalyl chloride $(COCl)_2$. It has now been discovered that $SOCl_2$ is not too harsh for use with reactants having an amido group, provides improved yields of the corresponding carboxylic acid chloride, and is thus preferred for use in step (a).

In a highly preferred mode, step (b) is conducted in a reaction medium which comprises a two-phase mixture of water and an organic solvent, most preferably using the reaction conditions disclosed hereinafter. The organic solvent is chosen from those which are compatible with (i.e., non-reactive with) the amino acid halide formed in step (a). Ether solvents, hydrocarbon solvents and the like are useful for this purpose. Alcohols, amines and other solvents which could react with the amino acid halide are avoided.

All percentages, ratios and proportions herein are by weight, unless otherwise specified. All documents cited are, in relevant part, incorporated herein by reference.

DETAILED DESCRIPTION OF THE INVENTION

The process herein is conducted using reagents and conditions as disclosed more fully hereinafter. The overall reaction sequence is shown below for the synthesis of the "NACA-OBS" activator.

Step (a): Prepare Acid Chloride of N-Nonanoyl-6-Aminocaproic Acid

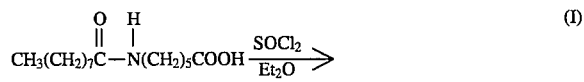

Step (b): React Acid Chloride with Na Phenol Sulfonate Under Schotten-Baumann conditions

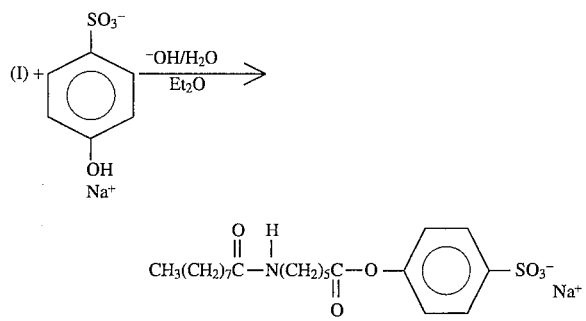

Step (a) of the reaction herein is conducted as noted hereinafter, typically at room temperature (15° C.–25° C.).

Step (b) of the reaction herein is conducted at about 5° C. to about 20° C. and at a pH range of about 9 to about 12.2, preferably about 10–11. It has now been discovered that this pH range for the reaction medium is critical to allow the phenol sulfonate reactant to be present in its anionic form, yet not be so alkaline as to hydrolyze the desired reaction product.

The reaction is virtually instantaneous, and can be monitored, if desired, by the pH drop in the aqueous solvent phase. As the pH drops, additional base is added to maintain the pH in the range noted.

EXAMPLE I

Synthesis of the Phenol Sulfonate Ester of N-Nonanoyl-6-Aminocaproic Acid (NACA-OBS)—Acid Chloride of N-Nonanoyl-6-Aminocaproic Acid—A one L round-bottomed flask equipped for magnetic stirring is charged with 27.1 g (0.100 mol) of N-nonanoyl-6-aminocaproic acid and 150 mL of diethyl ether. With stirring, 35.7 g (21.9 mL, 0.300 mol) of thionyl chloride is added in portions over a five minute period. The addition of the first few mLs of thionyl chloride causes the majority of the amido acid to dissolve. The resulting solution is stirred at room temperature for 10 minutes, and the ether and excess thionyl chloride are removed with a rotary evaporator. Removal of last traces of thionyl chloride is accomplished by twice adding 100 mL of iso-octane and stripping on a rotary evaporator. Following these procedures there remains 35.8 g of a pale-yellow oil. This product is assumed to consist of 0.100 mol of the acid chloride of N-nonanoyl-6-aminocaproic acid.

Phenol Sulfonate Ester of N-Nonanoyl-6-Aminocaproic Acid (Schotten-Baumann Conditions)—A 600 mL beaker equipped for mechanical stirring and fitted with a pH electrode is charged with 39.2 g (0.200 mol) of the sodium salt of p-phenol sulfonate and 200 mL of 1.0N sodium hydroxide solution. The resulting solution has a pH of 12.2. The solution is cooled in an ice bath and, with stirring, a solution of the acid chloride (prepared above) in 100 mL of diethyl ether is added dropwise over a 10 minute period. The pH of the solution drops rapidly as the acid chloride solution is added. When the pH drops below 9.0 a 50% solution of sodium hydroxide is added dropwise to maintain the pH above 9.0. Upon addition of the acid chloride the reaction mixture becomes thick with suspended solid. Following completion of addition of the acid chloride the reaction mixture is stirred in the cold for 10 minutes. At this point the reaction mixture is thick with suspended solid and the pH has stabilized at 9.2. The ice bath is removed and the suspended solid is collected by filtration. This solid (still wet with reaction solution) is dried in air and then under vacuum to yield 41.6 g of a white solid having a slight pink tint. Analysis by $^1$H NMR ($d_6$-DMSO solvent) reveals a composition of 75% by weight of the phenol sulfonate ester of N-nonanoyl-6-aminocaproic acid (NACA-OBS) and 25% sodium phenol sulfonate. Yield of NACA-OBS is 31.3 g (70% of theory).

Synthesis of the Phenol Sulfonate Ester of N-Nonanoyl-6-Aminocaproic Acid—Isolation by Centrifugation—The acid chloride and phenol sulfonate ester of N-nonanoyl-6-aminocaproic acid is prepared as described above. A weight of 74.0 g (0.273 mol) of amido acid gives 0.273 mol of the acid chloride as a light brown oil. This oil is dissolved in 100 mL of diethyl ether and reacted with 107.1 g (0.546 mol) of sodium phenol sulfonate under Schotten-Baumann conditions. At the end of the reaction period the pH of the solution is adjusted to 8.0 and the solid precipitate is collected via centrifugation (International Equipment Company, Boston, Mass., Model BE-50). The resulting solid is twice resuspended in water and collected by centrifugation. The resulting wet cake is freeze-dried to yield 60.1 g (49%) of the phenol sulfonate ester of N-nonanoyl-6-aminocaproic acid (NACA-OBS) as a white solid. NMR analysis indicated the sample is 94.8% pure, containing 2.8% sodium phenol sulfonate and 2.4% of the amido acid.

Perhydrolysis of the Phenol Sulfonate Ester of N-Nonanoyl-6-Aminocaproic Acid (NACA-OBS)—A 4 L Erlenmeyer flask is charged with 4 L of room-temperature distilled water, 1.20 g of anhydrous sodium carbonate, 0.040 g diethylenetriaminepentaacetic acid (Aldrich), 0.36 g of sodium perborate monohydrate, and 0.36 g of the sodium salt of the p-phenol sulfonate ester of N-nonanoyl-6-aminocaproic acid (screened through a 35 mesh (Tyler equivalent) screen and dispersed in 10 mL dimethylformamide). At regular intervals aliquots of the solution are removed and analyzed iodometrically for the presence of N-nonanoyl-6-aminoperoxycaproic acid. This analysis affords the concentration of the peroxy acid as ppm (pans per million) available oxygen (AvO). The results obtained are tabulated below (time=0 corresponds to addition of the DMF solution of the phenol sulfonate ester to the water solution of sodium carbonate, chelant, and sodium perborate).

| Perhydrolysis of Phenol Sulfonate Ester of N-Nonanoyl-6-Aminocaproic Acid (NACA-OBS) to Yield N-Nonanoyl-6-Aminoperoxycaproic Acid (NAPCA) | | |
|---|---|---|
| Time min. | ppm AvO found | % Theoretical AvO |
| 2 | 2.3 | 73 |
| 6 | 2.0 | 63 |
| 10 | 2.8 | 88 |
| 30 | 2.4 | 76 |

Preparation of the Phenol Sulfonate Ester of the Monononyl Amide of Adipic acid (NAAA-OBS)—The acid chloride of the mononylamide of adipic acid is prepared as described above for N-nonanoyl-6-aminocaproic acid. Thus, 54.3 g (0.200 mol) of the mononylamide of adipic acid is treated with 71.4 g (0.600 mol) of thionyl chloride in 150 mL of diethyl ether to yield 0.200 mol of the acid chloride. This acid chloride is reacted with 78.5 g (0.400) mol of sodium phenol sulfonate under aqueous alkaline conditions (Schotten-Baumann conditions). The resulting reaction mixture contained precipitated solid which is collected by filtration. After air dying this solid weighed 47.2 g and is shown by 1H NMR analysis to contain 78.8% of the phenol sulfonate ester of the mononynylamide of adipic acid (NAAA-OBS), 13.6% sodium phenol sulfonate, and 7.8% of the monononylamide of adipic acid. Yield of NAAA-OBS is 37.2 g (41%).

The foregoing NACA-OBS and NAAA-OBS materials can be formulated in combination with known bleaching ingredients such as percarbonate, persulfate, and other peroxy materials to provide cleaning compositions. Representative, but non-limiting, examples of such compositions are as follows.

EXAMPLE III

A granular bleach composition suitable for use in fabric laundering and general-purpose cleaning operations is as follows.

| Ingredient | % (wt.) |
| --- | --- |
| Sodium Percarbonate | 20.0 |
| NAAA-OBS | 7.0 |
| Sodium Sulfate | Balance |

A laundry detergent composition with activated bleach ingredients is as follows.

| Ingredient | % (wt.) |
| --- | --- |
| $C_{12-14}$ alkyl sulfate, Na | 7.0 |
| $C_{14-15}$ alcohol ethoxylate (EO 1.0) sulfate | 2.0 |
| Zeolite A (0.1–10 micron) | 28.0 |
| Sodium carbonate | 27.0 |
| Sodium sulfate | 12.0 |
| Sodium percarbonate | 6.0 |
| NACA-OBS | 3.0 |
| Sodium silicate | 3.0 |
| Citric acid | 2.0 |
| Sodium polyacrylate | 3.5 |
| Water and minors* | Balance |

*Includes optical brightener and protease, cellulase, lipase and amylase enzymes.

What is claimed is:

1. A process for preparing phenol sulfonate esters of hydrocarboyl amino acids, comprising the steps of:

(a) reacting an amino acid of the formula

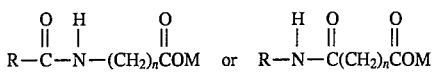

wherein n is from 1 to about 8, M is H or an alkali metal salt, and R is a $C_1$–$C_{14}$ alkyl, alkenyl, aryl or alkaryl substituent, with an acid halide to prepare the corresponding amino acid halide; and (b) reacting the amino acid halide of step (a) with a phenol sulfonate in the presence of water and base.

2. A process according to claim 1 wherein step (a) is conducted using an inorganic acid halide selected from the group consisting of $SOCl_2$, $PCl_3$, $PCl_5$, $POCl_3$ and their corresponding bromides, or oxaloyl chloride.

3. A process according to claim 2 wherein R is $C_7$–$C_9$ alkyl and wherein the acid halide of step (a) is $SOCl_2$.

4. A process according to claim 1 wherein step (b) is conducted at a pH in the range from about 9 to about 12.2.

5. A process according to claim 4 wherein step (b) is conducted at a pH from about 10 to about 11, and at a temperature of from about 5° C. to about 20° C.

6. A process according to claim 1 wherein step (b) is conducted in a two-phase reaction medium comprising water and an organic solvent which is compatible with said amino acid halide formed in step (a).

7. A process according to claim 1 for the preparation of the phenol sulfonate ester of N-nonanoyl-6-aminocaproic acid.

8. A process according to claim 1 for the preparation of the phenol sulfonate ester of the mononyl amide of adipic acid.

* * * * *